United States Patent [19]

Knowles

[11] Patent Number: 5,585,042

[45] Date of Patent: *Dec. 17, 1996

[54] PHOTOCHROMIC NAPHTHOPYRANS

[75] Inventor: David B. Knowles, Apollo, Pa.

[73] Assignee: Transitions Optical, Inc., Pinellas Park, Fla.

[*] Notice: The term of this patent shall not extend beyond the expiration date of Pat. No. 5,238,981.

[21] Appl. No.: 345,095

[22] Filed: Nov. 28, 1994

Related U.S. Application Data

[60] Continuation-in-part of Ser. No. 71,121, Jun. 2, 1993, Pat. No. 5,369,158, which is a division of Ser. No. 840,378, Feb. 24, 1992, Pat. No. 5,238,981.

[51] Int. Cl.$^6$ ............... G02B 5/23; G02B 27/00; C07D 311/92; C08K 5/15
[52] U.S. Cl. ............... 252/586; 549/389; 549/331; 524/110
[58] Field of Search .................. 549/389, 331; 252/586; 524/110

[56] References Cited

U.S. PATENT DOCUMENTS

| | | | |
|---|---|---|---|
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 3,627,690 | 12/1971 | Casella et al. | 549/389 |
| 4,215,010 | 7/1980 | Hovey et al. | 252/300 |
| 4,342,668 | 8/1982 | Hovey et al. | 252/586 |
| 4,563,458 | 1/1986 | Widdig et al. | 514/253 |
| 4,637,698 | 1/1987 | Kwak et al. | 351/163 |
| 4,720,356 | 1/1988 | Chu | 252/586 |
| 4,816,584 | 3/1989 | Kwak et al. | 544/71 |
| 4,818,096 | 4/1989 | Heller et al. | 351/163 |
| 4,826,977 | 5/1989 | Heller et al. | 544/70 |
| 4,931,221 | 6/1990 | Heller et al. | 252/586 |
| 5,066,818 | 11/1991 | Van Gemert | 549/389 |
| 5,200,116 | 4/1993 | Heller | 252/586 |
| 5,238,981 | 8/1993 | Knowles | 524/110 |
| 5,244,602 | 9/1993 | Van Gemert | 252/589 |
| 5,274,132 | 12/1993 | Van Gemert | 549/389 |
| 5,340,857 | 8/1994 | Van Gemert | 524/110 |
| 5,369,158 | 11/1994 | Knowles | 524/110 |
| 5,384,077 | 1/1995 | Knowles | 252/586 |
| 5,395,567 | 3/1995 | Van Gemert et al. | 252/586 |

FOREIGN PATENT DOCUMENTS

| | | |
|---|---|---|
| 246114 | 5/1987 | European Pat. Off. |
| 250193 | 6/1987 | European Pat. Off. |
| 294056 | 12/1988 | European Pat. Off. |
| 02-69471 | 3/1990 | Japan |

OTHER PUBLICATIONS

Padwa et al, J. Org. Chem., vol. 40, No. 8, 1975, pp. 1142–1149.

*Primary Examiner*—Nicky Chan
*Attorney, Agent, or Firm*—Frank P. Mallak; Irwin M. Stein

[57] ABSTRACT

Described are novel reversible photochromic naphthopyran compounds substituted at the number eight carbon atom on the naphtho portion of the naphthopyran ring with, for example, a methoxy group. Also described are polymeric organic host materials that contain or that are coated with such compounds. Optically clear articles such as ophthalmic lenses or other plastic transparencies that incorporate the novel naphthopyran compounds or combinations thereof with complementary photochromic compounds, e.g., certain spiro(indoline)type compounds, are also described.

22 Claims, No Drawings

PHOTOCHROMIC NAPHTHOPYRANS

This application is a continuation in part of application Ser. No. 08/071,121 filed Jun. 2, 1993, now U.S. Pat. No. 5,369,158 which is a division of application Ser. No. 07/840,378, filed Feb. 24, 1992, now U.S. Pat. 5,238,981.

DESCRIPTION OF THE INVENTION

The present invention relates to certain novel naphthopyran compounds. More particularly, this invention relates to novel photochromic naphthopyran compounds with unexpected properties, and to compositions and articles containing such novel naphthopyran compounds. When exposed to light radiation involving ultraviolet (UV) rays, such as the ultraviolet radiation in sunlight or the light of a mercury lamp, many photochromic compounds exhibit a reversible change in color. When the ultraviolet radiation is discontinued, the photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of chromene derivatives, including certain benzopyrans and naphthopyrans. These compounds are described as derivatives of chromene and are reported to undergo a color change, e.g., from colorless to yellow-orange, on irradiation by ultraviolet light at temperatures below about –40° C. Irradiation of the compounds with visible light or upon raising the temperature to within the range of –10° C. to 0° C. is reported to reverse the coloration to a colorless state. U.S. Pat. No. 4,931,221 describes a series of spiropyrans in which two cyclopropyl groups are appended to the position adjacent to the oxygen in the pyran ring. U.S. Pat. No. 4,563,458 describes certain 2H-chromenes as precursors of certain chroman-4-aldehydes, which are reacted with certain amines to prepare 4-aminomethylene-chromans and -chromenes that are used in medicaments.

European Patent Publication 246,114 and U.S. Pat. No. 4,826,977 describe a series of photochromic spiropyrans in which a spiro-adamantane group is appended to the position adjacent to the oxygen in the pyran ring. U.S. Pat. No. 4,818,096 and European Patent Publication 250,193 describe photoreactive plastic lenses that are coated or impregnated with the photochromic spiropyrans of European Patent Publication 246,114 in combination with a photochromic benzopyran or naphthopyran having an aminophenyl substituent at the position adjacent to the oxygen in the pyran ring. European Patent Publication 294,056 describes a process for producing a polyurethane plastic having photochromic properties. Reversible cleavage photochromic compounds disclosed therein include a naphthopyran derivative in which the pyran ring is substituted at the 3-position of the pyran ring with di(p-methoxyphenyl) substituents. Japanese Patent Publication HEI 2(1990)-69471 describes spiropyran compounds in which a norbornylidene group is substituted at the position adjacent to the oxygen in the pyran ring.

Padwa et al in *J. Org. Chem.*, Volume 40, No. 8, 1975, page 1142, describes the investigation of photochemical reactions of 2,2-dimethylbenzopyran and related compounds, identifies the by-products and suggests pathways to the ring-opened color intermediates and the final non-colored phenolics. The color forms examined by the authors are reported as being unstable at room temperature. The authors do not suggest ways in which the stability of the examined compounds might be improved, nor any modification that might be made to the structure of the known pyran compounds.

The present invention relates to novel naphthopyran compounds containing certain substituents at the number eight carbon atom on the naphtho portion of the naphthopyran. The absorption maxima of these compounds have been found to be unexpectedly higher than the corresponding unsubstituted compounds.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes have been of interest because of the potential safety features that such transparencies offer.

Ideal photochromic compounds for use in optical applications, such as conventional ophthalmic lenses, are those which possess (a) a high quantum efficiency for coloring, (b) a relatively fast change in optical density over time, (c) a high optical density at saturation, (d) a low quantum yield for bleaching with visible light and (e) a relatively fast thermal fade at ambient temperature but not so rapid a thermal fade rate that the combination of visible light bleaching and thermal fade prevent coloring by the ultraviolet component of strong sunlight. The aforesaid properties are desirably retained when the photochromic compound is applied to or incorporated within conventional rigid synthetic plastic materials customarily used for ophthalmic and plano lenses. A naphthopyran such as 3,3-diphenyl-3H-naphtho[2,1-b]pyran, changes color on exposure to ultraviolet; but, at room temperature and above, this compound changes optical density too slowly, has too low an optical density at saturation, and bleaches too rapidly for use in an ophthalmic lens.

In accordance with the present invention, there has been discovered certain novel reversible photochromic naphthopyran compounds with unexpected properties. These compounds are substituted at the number eight carbon atom on the naphtho portion of the naphthopyran, and exhibit a dramatic bathochromic shift of their absorption maximum in both the visible spectrum of the activated form and the UV spectrum of the unactivated form. The shift in the UV spectrum has contributed to an increase in sensitivity as measured by how fast the optical density of the compounds change with time, and to an increase in the compounds optical density, as measured by how dark they become, vis a vis, naphthopyrans substituted at the number five, seven or nine carbon atom of the naphtho portion of the naphthopyran. In particular, 3,3-diaryl-3H-naphtho-[2,1-b] pyrans that are appropriately substituted at the number eight carbon atom have a high quantum efficiency for coloring, good sensitivity and saturated optical density, and an acceptable bleach or fade rate. Such compounds are particularly suitable for use in ophthalmic applications.

Naphthopyran compounds contemplated to be within the scope of the present invention may be represented by the following graphic formula I:

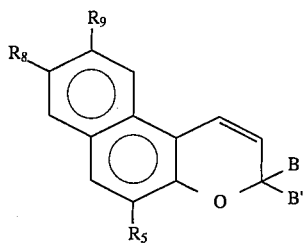

In graphic formula I, $R_5$ and $R_9$ are each selected from the group consisting of hydrogen, $C_1$–$C_4$ alkoxy, e.g., methoxy, and $C_1$–$C_4$ alkyl, e.g., methyl. More preferably, $R_5$ and $R_9$ are each selected from the group consisting of hydrogen, $C_1$–$C_3$ alkoxy, and $C_1$–$C_3$ alkyl. Most preferably, $R_5$ and $R_9$ are each selected from the group consisting of hydrogen, $C_1$–$C_2$ alkoxy, and $C_1$–$C_2$ alkyl. $R_8$ is selected from the group consisting of halogen, $C_1$–$C_5$ acyloxy, benzoyloxy, methoxybenzoyloxy, di($C_1$–$C_5$)alkylamino and LO—, wherein L is a $C_1$–$C_{12}$ alkyl, $C_6$–$C_9$ aryl($C_1$–$C_3$)alkyl, $C_5$–$C_7$ cycloalkyl, or $C_1$–$C_4$ alkyl substituted $C_5$–$C_7$ cycloalkyl. The $C_6$–$C_9$ moiety of the $C_6$–$C_9$ aryl($C_1$–$C_3$)alkyl group comprises unsubstituted and alkyl-substituted benzene groups, i.e., mono-, di-, or tri-, alkyl substituted benzene. $R_8$ may also be selected from a group having cyclic amino containing saturated members such as piperidino, pyrrolidino, and morpholino or from a group having benz-fused nitrogen containing heterocyclics such as indolino, substituted and unsubstituted dihydroindolino, said substituents being $C_1$–$C_3$ alkyl. Preferably, $R_8$ is chloro, bromo, $C_1$–$C_4$ acyloxy, benzoyloxy, methoxybenzoyloxy, di($C_1$–$C_4$) alkylamino, and LO wherein L is a $C_1$–$C_{10}$ alkyl, $C_6$–$C_7$ aryl($C_1$–$C_2$)alkyl, $C_5$–$C_6$ cycloalkyl, or $C_1$–$C_3$ alkyl substituted $C_5$–$C_6$ cycloalkyl. More preferably, $R_8$ is bromo, $C_1$–$C_3$ acyloxy, di($C_1$–$C_3$) alkylamino, and LO wherein L is a $C_1$–$C_4$ alkyl or $C_1$–$C_2$ alkyl substituted $C_5$–$C_6$ cycloalkyl. Most preferably, $R_8$ is methoxy.

In graphic formula I, B is selected from the group consisting of unsubstituted, mono-, di-, and tri-substituted phenyl, said substituents being selected from the group consisting of $C_1$–$C_4$ alkyl, $C_1$–$C_4$ haloalkyl, $C_1$–$C_4$ alkoxy, $C_1$–$C_4$ alkoxy($C_1$–$C_4$)alkyl, di-($C_1$–$C_5$)alkylamino, and halogen, said halogen (halo) substituents being fluorine, chlorine, or bromine. Preferably, B is phenyl or substituted phenyl, e.g., mono- or di-($C_1$–$C_4$)alkyl substituted phenyl, such as methylphenyl; mono- or di-($C_1$–$C_4$)alkoxy substituted phenyl, such as methoxyphenyl; and halophenyl, such as chlorophenyl and fluorophenyl. The phenyl substituents may be located at the ortho, meta, and/or para positions. Typically, the substituted phenyl contains less than 3 substituents, i.e., zero (none), one or two substituents. More preferably, B is phenyl or the substituted phenyl group represented by the following graphic formula I-A:

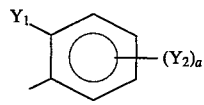

wherein $Y_1$ may be selected from the group consisting of $C_1$–$C_5$ alkyl, e.g., methyl, ethyl, propyl, butyl and pentyl, $C_1$–$C_5$ alkoxy, e.g., methoxy, ethoxy, propoxy, butoxy and pentoxy, fluoro and chloro, preferably $C_1$–$C_3$ alkyl, $C_1$–$C_3$ alkoxy and fluoro; $Y_2$ may be selected from the group consisting of $C_1$–$C_5$ alkyl, $C_1$–$C_5$ alkoxy, cyano, hydroxy, halogen, preferably chloro or fluoro, acrylyl, methacrylyl, acryloxy ($C_1$–$C_4$) alkyl, and methacryloxy ($C_1$–$C_4$) alkyl. Preferably, $Y_2$ is selected from the group consisting of $C_1$–$C_3$ alkyl, $C_1$–$C_3$ alkoxy and fluoro. In a particular embodiment, $Y_2$ is $C_1$–$C_3$ alkyl or $C_1$–$C_3$ alkoxy; and a is an integer of from 0 to 2; preferably a is 0 or 1. The positioning of the $Y_2$ substituent is preferably in the 3, 4 or 5 positions. When a is 1, the preferred position is meta or para to the carbon atom attached to the pyran ring. When a is 2, the positions are preferably at the 3 and 4, 3 and 5, or 4 and 5 numbered carbon atoms.

B' is selected from the group consisting of (i) $C_1$–$C_6$ alkyl, $C_1$–$C_6$ haloalkyl, $C_1$–$C_6$ alkoxy($C_1$–$C_4$)alkyl, said halo group being fluoro or chloro; and (ii) the group represented by the following graphic formula I-B:

wherein X in graphic formula I-B may be hydrogen or $C_1$–$C_4$ alkyl and Z in graphic formula I-B may be selected from the unsubstituted, mono-, and di-substituted members of the group consisting of naphthyl, phenyl, furanyl, and thienyl, said group substituents being $C_1$–$C_4$ alkyl, $C_1$–$C_4$ alkoxy, fluoro, or chloro.

More preferably B' is selected from the group consisting of (i) $C_1$–$C_4$ alkyl; and (ii) the group represented by the graphic formula I-B wherein X is hydrogen or methyl and Z is phenyl or mono-substituted phenyl, said phenyl substituents being selected from the group consisting of $C_1$–$C_3$ alkyl, $C_1$–$C_3$ alkoxy, and fluoro.

B and B' taken together may form an unsubstituted, mono-, or di-substituted fluoren-9-ylidene or form a member selected from the group consisting of saturated $C_3$–$C_{12}$ spiro-monocyclic hydrocarbon rings, e.g., cyclopropylidene, cyclobutylidene, cyclopentylidene, cyclohexylidene, cycloheptylidene, cyclooctylidene, cyclononylidene, cyclodecylidene, cycloundecylidene, cyclododecylidene, saturated $C_7$–$C_{12}$ spiro-bicyclic hydrocarbon rings, e.g., bicyclo[2.2.1]heptylidene, i.e., norbornylidene, 1,7,7-trimethyl bicyclo[2.2.1]heptylidene, i.e., bornylidene, bicyclo[3.2.1]octylidene, bicyclo[3.3.1]nonan-9-ylidene, bicyclo[4.3.2]undecane, and saturated $C_7$–$C_{12}$ spiro-tricyclic hydrocarbon rings, e.g., tricyclo[2.2.1.0$^{2,6}$]heptylidene, and tricyclo[5.3.1.1$^{2,6}$]dodecylidene, provided that B and B' do not form the tricyclo[3.3.1$^{3,7}$]decylidene, i.e., adamantylidene, said fluoren-9-ylidene substituents being selected from the group consisting of $C_1$–$C_4$ alkyl, $C_1$–$C_4$ alkoxy, fluoro and chloro.

More preferably, B and B' taken together form an unsubstituted or mono-substituted fluoren-9-ylidene or a member selected from the group consisting of saturated $C_3$–$C_8$ spiro-monocyclic hydrocarbon rings, saturated $C_7$–$C_{10}$ spirobicyclic hydrocarbon rings, and saturated $C_7$–$C_{10}$ spiro-tricyclic hydrocarbon rings. Most preferably, B and B' taken together form fluoren-9-ylidene, bornylidene, norbornylidene, or bicyclo[3.3.1]nonan-9-ylidene.

Compounds represented by graphic formulae I may be prepared by various synthetic routes. For example, the reaction of 2,6-dihydroxynaphthalene with an appropriate reagent, e.g., dimethyl sulfate will yield the corresponding substituted hydroxynaphthalene e.g., 6-methoxy-2-hydroxynaphthalene. The intermediate 6-substituted-2-hydroxynaphthalene may then be reacted further with the appropriate disubstituted, i.e., B,B'-substituted, propargyl alcohol, e.g., 1-phenyl-1-butyl-2-propyn-1-ol, under acidic conditions to form compounds of graphic formula I. Such disubstituted propargyl alcohols may be prepared from commercially available ketones or ketones prepared via reaction of an acyl halide with a substituted or unsubstituted benzene. Propargyl alcohols having the B' group represented by graphic formula I-B may be prepared by the methods described in U.S. Pat. No. 5,274,132, column 2, lines 40 to 68. Because of the limited availability of 2,6-dihydroxynaphthalene, it is contemplated that other substituted dihydroxynaphthalene starting reagents, i.e, 2,3-dihydroxynaphthalene-6-sulfonic acid sodium salt and 2,7-dihydroxynaphthalene-3-6-disulfonic acid disodium salts, which are more readily available in commercial quantities, may be used to synthesize the compounds of graphic formula I. The presence of an alkoxy group, e.g., methoxy, on the number 5 and/or 9 carbon atoms of the resulting naphthopyran compound does not affect the unexpected photochromic properties observed for the naphthopyran compounds having the described substituents on the number 8 carbon atom. It is also contemplated that other starting dihydroxynaphthalene reagents which result in substituents on the naphtho portion of the naphthopyran (in addition to the desired substituent on the number 8 carbon atom) that do not affect the observed unexpected bathochromic shift of the absorption maximum may be used to synthesize the naphthopyran compounds of graphic formula I.

Compounds represented by graphic formula I may be used in those applications in which organic photochromic substances may be employed, such as optical lenses, e.g., vision correcting ophthalmic lenses and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired. Naphthopyrans represented by graphic formula I exhibit color changes from colorless to colors ranging from yellow to orange.

Of particular current interest are the following naphthopyrans:

(1) 8-methoxy-3-phenyl-3-t-butyl-3H-naphtho [2,1-b]pyran;

(2) 8-methoxy-3-(2-fluorophenyl)-3-(2-phenylvinyl)-3H-naphtho [2,1-b]pyran;

(3) 8-methoxy-3-(4-trifluoromethylphenyl)-3-(2-phenyl-1-methylvinyl)-3H-naphtho [2,1-b]pyran;

(4) 8-methoxy-3-(4- dimethylaminophenyl)-3-(2-(2-thienyl) vinyl)-3H-naphtho [2,1-b]pyran;

(5) 5,8-dimethoxy-3-phenyl-3-t-butyl-3H-naphtho [2,1-b]pyran; and (6) 8-bromo-3-phenyl-3-(2-phenylvinyl)-3H-naphtho naphtho [2,1-b]pyran.

Commercially available photoreactive inorganic glass ophthalmic lenses containing silver halide particles darken to a gray or brown color in sunlight. In order to duplicate this color change in a plastic lens using the organic photochromic naphthopyrans of graphic formula I, it is contemplated that such naphthopyrans be used in combination with other appropriate complementary organic photochromic materials so that together they produce the desired near neutral gray or brown color shade when the plastic lens containing such photochromic materials are exposed to ultraviolet light. For example, a compound which colors to yellow may be blended with a compound that colors to an appropriate purple to produce a brown shade. Similarly, a compound which is orange in its colored state will produce a shade of gray when used in conjunction with an appropriate blue coloring compound. The aforesaid described combination of photochromic materials may be used also in applications other than ophthalmic lenses.

The novel naphthopyran compounds of the present invention, such as those heretofore described, may be used alone or in combination with complementary photochromic compounds, i.e., organic photochromic compounds having at least one activated absorption maxima within the range of between about 400 and 700 nanometers, or substances containing same, and may be incorporated, e.g., dissolved or dispersed, in a polymeric organic host material used to prepare photochromic articles and which color when activated to an appropriate hue.

A first group of complementary organic photochromic substances contemplated for use with the organic photochromic naphthopyrans of the present invention are those having an activated absorption maximum within the visible range of greater than 570 nanometers, e.g., between about greater than 570 to 700 nanometers. These materials typically exhibit a blue, blueish-green, or blueish-purple color when exposed to ultraviolet light in an appropriate solvent or matrix. Many of such compounds are described in the open literature. For example, spiro(indoline)naphthoxazines have been described, among others, in U.S. Pat. Nos. 3,562,172; 3,578,602; 4,215,010; and 4,342,668; spiro(indoline)naphthoxazines having certain substituents on the 8' and 9' positions of the naphthoxazine portion of the molecule are the subject of copending U.S. patent application Ser. No. 07/993,587, filed Dec. 21, 1992; spiro(indoline)pyridobenzoxazines are described in U.S. Pat. No. 4,637,698; spiro(benzindoline)pyridobenzoxazines and spiro(benzindoline)naphthoxazines are described in U.S. Pat. No. 4,931,219; spiro(benzindoline)naphthopyrans are described in Japanese Patent Publication 62/195383; spiro(indoline)benzoxazines are described in U.S. Pat. No. 4,816,584; spiro(indoline)benzopyrans, spiro(indoline)naphthopyrans, and spiro(indoline)quinopyrans are described, for example, in U.S. Pat. No. 4,880,667; and benzopyrans and naphthopyrans having a nitrogen-containing substituent in the 2-position of the pyran ring are described in U.S. Pat. No. 4,818,096. Spiro(indoline)pyrans are also described in the text, *Techniques in Chemistry*, Volume III, "Photochromism," Chapter 3, Glenn H. Brown, Editor, John Wiley and Sons, Inc., New York, 1971.

A second group of complementary organic photochromic substances contemplated for use with the organic photochromic naphthopyrans of the present invention are those having an absorption maximum within the visible range of between about 400 to about 500 nanometers and another absorption maximum within the visible range of between about 500 to about 700 nanometers. These materials typically exhibit color(s) ranging from yellow to purple and yellow/brown to purple/gray when exposed to ultraviolet light in an appropriate solvent or matrix. Examples of these compounds include certain substituted 2H-phenanthro[4,3-b]pyrans; substituted 3H-phenanthro[1,2-b]pyrans; and benzopyran compounds, such as those having substituents at the 2-position of the pyran ring and a substituted or unsubstituted heterocyclic ring, such as a benzothieno or benzofurano ring fused to the benz portion of the benzopyran. Such later described compounds are the subject of co-pending U.S. patent application Nos. 08/286,039 filed Aug. 4, 1994 and 08/201,948, filed Feb. 24, 1994.

A third group of complementary organic photochromic substances contemplated for use with the organic photochromic naphthopyrans of the present invention are those having at least one absorption maximum within the visible range of between about 400 and less than 500 nanometers. These materials typically exhibit a yellow-orange color when exposed to ultraviolet light in an appropriate solvent or matrix. Such compounds include certain chromenes, i.e., benzopyrans and naphthopyrans. Many of such chromenes are described in the open literature, e.g., U.S. Pat. Nos. 3,567,605; 4,826,977; and 5,066,818. Other examples of complementary benzopyrans and naphthopyrans that may be used with the naphthopyrans of the present invention include: those having a spiro adamantane group at the position alpha to the oxygen atom of the pyran ring, which are described in U.S. Pat. No. 4,826,977; 2H-naphtho-[1,2-b]pyran compounds having certain substitutents at the number 5 and 6 carbon atoms of the naphtho portion of the naphthopyran and at the 2 position of the pyran which are the subject of co-pending U.S. patent application Ser. No. 08/164,187, filed Dec. 9, 1993; 3H-naphtho[2,1-b]pyrans having at least one ortho-substituted phenyl substituent at the 3-position of the pyran ring which are described in U.S. Pat. No. 5,066,818; 3H-naphtho[2,1-b]pyran compounds having certain substituents at the number 8 carbon atom and certain substituents being on the number 7 or 9 carbon atom, all substituents being on the naphtho portion of the naphthopyran, which are the subject of co-pending U.S. patent application Ser. No. 08/080,246, filed Jun. 21, 1993; 3H-naphtho[2,1-b]pyrans substituted at the 3 position of the pyran ring with (i) an aryl substituent and (ii) a phenyl substituent having a 5- or 6-member heterocyclic ring fused at the number 3 and 4 carbon atoms of the phenyl substituent which are the subject of co-pending U.S. patent application Ser. No.08/080,250 filed Jun. 21, 1993; diaryl-3H-naphtho [2,1-b]pyran compounds having a substituted or unsubstituted, 5 or 6 member heterocyclic ring fused to the g, i, or l side of the naphthopyran which are the subject of co-pending U.S. patent application Ser. No.08/225,022 filed Apr. 8, 1994; naphthopyran compounds substituted at the number 8 carbon atom on the naphtho portion of the naphthopyran ring, with for example, a methoxy group which are the subject of U.S. Pat. No. 5,238,931; naphthopyran compounds, examples of which are 3-aryl-3-arylalkenyl naphthopyrans, which are described in U.S. Pat. No. 5,274,132; and naphtho[2,1-b]pyrans substituted at the number five carbon atom with, for example, an acetoxy group, which are the subject of U.S. Pat. No. 5,244,602.

Photochromic articles of the present invention may contain one photochromic compound or a mixture of photochromic compounds, as desired or required. Individual photochromic compounds or mixtures of photochromic compounds may be used to attain certain activated colors such as neutral grays or browns.

The compounds of the present invention (hereinafter also referred to and included as a third group photochromic compound) may be used also in combination with the organic photochromic substances of the first complementary group of photochromic compounds described herein, i.e., those that color to colors blue, blueish-green, or blueish-purple with the organic photochromic substances of the second complementary group of photochromic compounds described herein that exhibit colors ranging from yellow to purple and yellow/brown to purple/gray and/or with other organic photochromic substances of the third complementary group of photochromic compounds described herein that exhibit the colors yellow/orange.

Each of the photochromic substances described herein may be used in amounts (or in a ratio) such that an organic host material to which the photochromic compounds or mixture of compounds is applied or in which they are incorporated exhibits a desired resultant color, e.g., a substantially neutral color when activated with unfiltered sunlight, i.e., as near a neutral color as possible given the colors of the activated photochromic compounds.

A neutral gray color exhibits a spectrum that has relatively equal absorption in the visible range between 400 and 700 nanometers. A neutral brown color exhibits a spectrum in which the absorption in the 400–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., $x=X/(X+Y+Z)$ and $y=Y/(X+Y+Z)$. Color as described in the CIE system can be plotted on a chromaticity diagram, usually a plot of the chromaticity coordinates x and y. See pages 47–52 of *Principles of Color Technology*, by F. W. Billmeyer, Jr., and Max Saltzman, Second Edition, John Wiley and Sons, N.Y. (1981). As used herein, a near neutral color is one in which the chromaticity coordinate values of "x" and "y" for the color are within the following ranges (D65 illuminant):x=0.260 to 0.400, y =0.280 to 0.400 following activation to 40 percent luminous transmission by exposure to solar radiation (Air Mass 1 or 2).

The amount of photochromic substance or composition containing same applied to or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic substance incorporated into or applied to a photochromic optical host material may range from about 0.05 to about 1.0, e.g., from 0.1 to about 0.45, milligrams per square centimeter of surface to which the photochromic substance(s) is incorporated or applied. When mixtures of the aforedescribed organic photochromic complementary groups are used, the weight ratio of such materials, i.e., (first to third), (second to third), and (naphthopyran of the present invention to other third group compounds) will vary from about 1:3 to about 3:1, e.g., between about 0.75:1 and about 2:1. The combination of the first, second, and third described organic photochromic complementary groups may have a weight ratio that will vary from about 1:3:1 to 3:1:3.

The photochromic substances of the present invention is may be applied to or incorporated into a host material such as a polymeric organic host material by various methods described in the art. Such methods include dissolving or dispersing the photochromic substance within the host material, e.g., casting it in place by adding the photochromic substance to the monomeric host material prior to polymerization; imbibition of the photochromic substance into the host material by immersion of the host material in a hot solution of the photochromic substance or by thermal transfer; providing the photochromic substance as a separate layer between adjacent layers of the host material, e.g., as a part of a polymeric film; and applying the photochromic substance as part of a coating placed on the surface of the host material. The term "imbibition" or "imbibe" is intended to mean and include permeation of the photochromic substance alone into the host material, solvent assisted transfer of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

Adjuvant materials may also be incorporated into the host material with the photochromic substances prior to, simultaneously with or subsequent to application or incorporation of the photochromic substances in the host material. For example, ultraviolet light absorbers may be admixed with photochromic substances before their application to the host material or such absorbers may be superposed, e.g., superimposed, as a layer between the photochromic substance and the incident light. Further, stabilizers may be admixed with the photochromic substances prior to their application to the host material to improve the light fatigue resistance of the photochromic substances. Stabilizers, such as hindered amine light stabilizers and singlet oxygen quenchers, e.g., a nickel ion complex with an organic ligand, are contemplated. They may be used alone or in combination. Such stabilizers are described in U.S. Pat. No. 4,720,356. Finally, appropriate protective coating(s) may be applied to the surface of the host material. These may be abrasion resistant coatings and/or coatings that serve as oxygen barriers. Such coatings are known in the art.

Singlet oxygen quenchers that may be used as stabilizers include complexes of nickel(2+), i.e., $Ni^{2+}$, with an organic ligand, cobalt (III) tris-di-n-butyldithiocarbamate, cobalt (II) diisopropyldithiocarbamate, and nickel diisopropyldithiophosphate. Such singlet oxygen quenchers are used in stabilizing amounts.

Preferred are complexes of $Ni^{2+}$ such as [2,2-thiobis[4-(1,1,3,3-tetramethylbutyl) phenolato](butylamine)]nickel, which is sold under the tradename CYASORB UV 1084; nickel [O-ethyl(3,5-di-tert-butyl-4-hydroxybenzyl)]phosphonate, which is sold under the tradename IRGASTAB 2002; nickel dibutyldithiocarbamate, which is sold under the tradename RYLEX NBC; bis[2,2'-thiobis-4-(1,1,3,3-tetramethylbutyl)phenolato]nickel, which is sold under the tradename UV-CHEK AM 101; nickel di-isopropyl dithiophosphate and other $Ni^{2+}$ complexes sold under the tradenames of UV-CHEK AM 105, UV-CHEK 126, and UV-CHEK AM 205.

Hindered amine light stabilizers that may be used include bis(2,2,6,6-tetramethyl-4-piperidinyl) sebacate, which is sold under the tradename TINUVIN 770; bis(1,2,2,6,6-penta-methyl-4-piperidinyl)sebacate, which is sold under the tradename TINUVIN 765; di(1,2,2,6,6-pentamethyl-4-piperidinyl)butyl-(3',5'-ditertiarybutyl-4-hydroxy-benzyl) malonate, which is sold under the tradename TINUVIN 144; poly[(6-[(1,1,3,3-tetramethylbutyl)amino]-1,3,5-triazine-2,4-diyl)-(6-[2,2,6,6-tetramethyl-4-piperidinyl]-amino-hexamethylene)], which is sold under the tradename CHIMASSORB 944; and poly[[6-(morpholino)-s-triazine-2,4-diyl][16-(2,2,6,6-tetramethyl-4-piperdyl)amino]hexamethylene], which is sold under the tradename CYASORB 3346. Other hindered amine light stabilizers that may be used are those sold under the tradename TINUVIN 622, SPINUVEX A-36 and HOSTAVIN TMN 20. Such stabilizers are used in stabilizing amounts.

The foregoing singlet oxygen quenchers and hindered amine light stabilizers may be used singly or in combination in amounts sufficient to enhance the light-fatigue resistance of the photochromic substance(s) described herein. Between 0.01 and about 5 percent by weight of the foregoing stabilizers may be used (alone or in combination) to improve the light fatigue resistance of the photochromic materials.

The host material will usually be transparent, but may be translucent or even opaque. The host material need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Preferably, the host color should not be such that it masks the color of the activated form of the photochromic substance, i.e., so the change in color is readily apparent to the observer. More preferably, the host material article is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

Examples of polymeric organic host materials which may be used with the photochromic substances or compositions described herein include: polymers, i.e., homopolymers and copolymers, of polyol(allyl carbonate) monomers, diethylene glycol dimethacrylate monomers, diisopropenyl benzene monomers, and alkoxylated polyhydric alcohol acrylate monomers such as ethoxylated trimethylol propane triacrylate monomers; polymers, i.e., homopolymers and copolymers, of polyfunctional, i.e., mono-, di-, tri-, tetra, or multifunctional, acrylate and/or methacrylate monomers, polyacrylates, polymethacrylates, poly($C_1$–$C_{12}$ alkyl methacrylates) such as poly(methyl methacrylate), polyoxy(alkylene methacrylates) such as poly(ethylene glycol bis methacrylates), poly(alkoxylated phenol methacrylates) such as poly(ethoxylated bisphenol A dimethacrylate), cellulose acetate, cellulose triacetate, cellulose acetate propionate, cellulose acetate butyrate, poly(vinyl acetate), s poly(vinyl alcohol), poly(vinyl chloride), poly(vinylidene chloride), polyurethanes, thermoplastic polycarbonates, polyesters, poly(ethytene terephthalate), polystyrene, poly (alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers.

Transparent copolymers and blends of transparent polymers are also suitable as host materials. Preferably, the host material is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis(allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. No. 4,360,653 and 4,994,208; and copolymers with aliphatic urethanes, the terminal portion of which contain allyl or acrylyl functional groups as described in U.S. Pat. No. 5,200,483; poly(vinyl acetate), polyvinylbutyral, polyurethane, polymers of members of the group consisting of diethylene glycol dimethacrylate monomers, diisopropenyl benzene monomers, and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile. More particularly, contemplated is use of the photochromic naphthopyrans of the present invention with optical organic resin monomers used to produce optically clear polymerizates, i.e., materials suitable for optical applications, such as for example plano and ophthalmic lenses, windows, and automotive transparencies. Such optically clear polymerizates may have a is refractive index that may range from about 1.48 to about 1.75, e.g., from about 1.495 to about 1.66.

The present invention is more particularly described in the following examples which are intended as illustrative only, since numerous modifications and variations therein will be apparent to those skilled in the art.

EXAMPLE 1

A reaction flask was charged with 200 milliliters (ml) of acetone, 13.8 grams (g) (0.1 mole) of powdered potassium carbonate and 16.0 g (0.1 mole) of 2,6-dihydroxynaphthalene. 12.6 g (0.1 mole) of dimethylsulfate was added dropwise and the reaction mixture was stirred at room temperature for 72 hours under a nitrogen atmosphere. 200 ml of a 10% aqueous sodium hydroxide solution was then added to the reaction flask. A white precipitate that formed, was removed by vacuum filtration. The aqueous filtrate was acidified with hydrochloric acid to a pH of 3 and the aqueous solution extracted three times—each time with 100 ml of methylene chloride. The extracts were combined, dried over anhydrous magnesium sulfate for 10 minutes and the solvent removed under vacuum. The remaining solid was washed with hot water—yielding 3.0 g of a solid product, which was confirmed by NMR spectroscopy to be 6-methoxy-2-hydroxynaphthalene.

1.1 g (0.006 mole) of the aforedescribed product, 6-methoxy-2-hydroxynaphthalene, was added to a reaction flask containing 100 ml of benzene and 1.3 g (0.006 mole of 1,1-diphenyl-2-propyn-1-ol. A catalytic amount (approximately 20.0 milligrams) of p-toluene sulfonic acid was added, the resulting mixture stirred and placed under a nitrogen atmosphere. The reaction mixture was heated gently at 50° C. for 4 hours, and then 200 ml of a 10% aqueous sodium hydroxide solution was added to the reaction flask. After stirring for 15 minutes, the reaction mixture was extracted twice—each time with 100 ml of methylene chloride. The extracts were combined, dried over anhydrous magnesium sulfate and the solvent removed under vacuum. The product (1.0 grams) melted at 173°–175° C. An NMR spectrum confirmed the product to be 8-methoxy-3,3-diphenyl-3H-naphtho [2,1-b]pyran.

EXAMPLE 2

A reaction flask was charged with 8.0 g of 2-fluoro-4'-methoxybenzophenone, (prepared by the Friedel-Crafts reaction of 2-fluorobenzoylchloride with anisole) in 150 ml of tetrahydrofuran and 14.0 g (1.5 equivalents) of sodium acetylide. The reaction mixture was stirred under a nitrogen atmosphere for 72 hours, cooled by pouring it into a 500 ml beaker containing ice water and extracted three times—each time with 100 ml of methylene chloride. The extracts were combined, dried over anhydrous magnesium sulfate and the solvent removed by vacuum. The product (7.0 g) was a yellow oil. The structure was confirmed by NMR to be 1-(2-fluorophenyl)-1-(4-methoxyphenyl)-2-propyn-1-ol.

2.4 g (0.008 mole) of the aforedescribed product, 1-(2-fluorophenyl)-1-(4-methoxyphenyl)-2-propyn-1-ol, was added to a reaction flask containing 100 ml of benzene and 1.4 g (0.008 mole) of 6-methoxy-2-hydroxynaphthalene. A catalytic amount of p-toluene sulfonic acid (approximately 20.0 milligrams) was added and the resulting mixture stirred and heated between 30°–35° C. under a nitrogen atmosphere for 3 hours. The reaction mixture was transferred to a solution containing 20% aqueous sodium hydroxide and extracted three times—each time with 100 ml of methylene chloride. The extracts were combined, dried over anhydrous magnesium sulfate and the solvent removed under vacuum. The resultant oil was column chromatographed on silica using 1:10 mixture of ethyl acetate:hexane as the elutant and crystallized by cooling in diethyl ether. The product (0.5 g) melted at 120°–123° C. An NMR spectrum confirmed the product to be 8-methoxy-3-(2-fluorophenyl)-3-(4-methoxyphenyl)-3H-naphtho[2,1-b]pyran.

EXAMPLE 3

A reaction flask was charged with 5 g (0.025 mole) of 4-methylbenzophenone, (prepared by the Friedel-Crafts reaction of benzoylchloride with toluene) in 200 ml of tetrahydrofuran and with 8.2 g (0.03 mole) of sodium acetylide. The reaction mixture was stirred under a nitrogen atmosphere for 8 hours, after which the reaction mixture was quenched in ice water and extracted three times—each time with 100 ml of diethyl ether. The extracts were combined, dried over anhydrous magnesium sulfate, and the solvent removed under vacuum. The product (5.0 g) was confirmed by NMR spectroscopy to be 1-phenyl-1-(4-methylphenyl)-2-propyn-1-ol.

5.0 g (0.02 mole) of the aforedescribed product, 1-phenyl-1-(4-methylphenyl)-2-propyn-1-ol, was added to a reaction flask containing 3.0 g (0.02 mole) of 6-methoxy-2-hydroxynaphthalene and 200 ml of benzene. The mixture was stirred under a nitrogen atmosphere, at 35° C. for 4 hours. The solvent was removed on a rotary evaporator and the resulting crude oil was washed with 200 ml of a 10% aqueous sodium hydroxide solution. The aqueous phase was ms extracted three times—each time with 100 ml of diethyl ether. The extracts were combined and dried over anhydrous magnesium sulfate for 15 minutes. The solvent was removed under vacuum and the resulting oil was crystallized using an ether-hexane mixture. The product crystals (3.0 g) melted at 169°–171° C. An NMR spectrum confirmed the product to be 8-methoxy-3-phenyl-3-(4-methylphenyl)-3 H-naphtho [2,1-b]pyran.

EXAMPLE 4

A reaction flask was charged with 5.0 g (0.02 mole) of 4-trifluoromethylbenzophenone, 200 ml of tetrahydrofuran and 6.7 g (0.024 mole) of sodium acetylide. The reaction mixture was stirred for 72 hours under a nitrogen atmosphere at room temperature and then was poured into a 500 ml beaker containing ice water and stirred for an additional thirty minutes. The aqueous phase was extracted three times—each time with 100 ml of diethyl ether. The extracts were combined and dried over anhydrous magnesium sulfate for 5 minutes. The solids were filtered and the solvent removed under vacuum. The product (2.75 g) was a yellow oil. The structure was confirmed by NMR spectroscopy to be 1-phenyl-1-(4-trifluoromethylphenyl)-2-propynl-1-ol.

2.75 g(0.01 mole) of the aforedescribed product, 1-phenyl-1-(4-trifluoromethylphenyl)-2-propynl-1-ol, was added to a reaction flask containing 1.9 g (0.01 mole) of 6-methoxy-2-hydroxynaphthalene and 200 ml of benzene. A catalytic amount (approximately 20.0 milligrams) of p-toluene sulfonic acid was added and the mixture was heated to 35° C. with stirring under a nitrogen atmosphere for 10 hours. The reaction mixture was transferred to a 500 ml beaker containing a 10% aqueous sodium hydroxide solution and stirred for an additional thirty minutes. The organic layer was separated and the aqueous layer extracted twice—each time with 100 ml of methylene chloride. The extracts were combined and dried over anhydrous magnesium sulfate for 10 minutes. After filtering off the solids, the solvent was removed under vacuum to yield 3.0 g of an oil. This oil was column chromatographed on silica gel using 20% ethyl acetate-hexane as the elutant. The solvent was removed under vacuum and the product was crystallized from hexane. The product (0.5 g) melted at 155°–157° C. The structure was confirmed by NMR spectroscopy to be 8-methoxy-3-phenyl-3-(4-trifluoromethylphenyl)-3H-naphtho[2,1-b]pyran.

EXAMPLE 5

A reaction flask was charged with 5.5 g (0.023 mole) of 2-fluoro-4'-methylbenzophenone, (prepared by the Friedel-Crafts reaction of 2-fluorobenzoylchloride with toluene) in 200 ml of tetrahydrofuran and with 7.5 g (0.023 mole) of sodium acetylide. The reaction mixture was stirred for 24 hours, then quenched with ice water and stirred for an additional thirty minutes. The organic phase was separated and the aqueous phase was extracted three times—each time with 100 ml of methylene chloride. The extracts were combined and washed with distilled water until clear. The extracts were dried over anhydrous magnesium sulfate, and the solvent removed under vacuum. The product (5.5 g) was a yellow oil. NMR spectroscopy confirmed the product to be 1-(2-fluorophenyl)-1-(4-methylphenyl)-2-propyn-1-ol.

5.5 g (0.023 mole) of the aforedescribed product, 1-(2-fluorophenyl)-1-(4-methylphenyl)-2-propyn-1-ol, was added to a reaction flask containing 4.0 g (0.023 mole) of 6-methoxy-2-hydroxynaphthalene and 200 ml of benzene. A catalytic amount (approximately 20.0 milligrams) of p-toluene sulfonic acid was added with stirring and the reaction was heated at 40° C. under a nitrogen atmosphere for 6 hours. The reaction mixture was transferred to a beaker containing 200 ml of a 10% aqueous sodium hydroxide solution and stirred for 15 minutes. The organic phase was separated and the aqueous phase washed twice—each time with 100 ml of methylene chloride. The extracts were combined, dried over anhydrous magnesium sulfate and the solvent removed under vacuum. The resultant oil was column chromatographed on silica gel using 20% ethyl acetate-hexane as the elutant. The photochromic fractions were collected and the solvent removed under vacuum. The product (2.0 g) melted at 157°–160° C. NMR spectroscopy confirmed the product to be 8-methoxy-3-(2-fluorophenyl)-3-(4-methylphenyl)-3H-naphtho[2,1-b]pyran.

EXAMPLE 6

A reaction flask was charged with 5.0 g (0.02 mole) of 4-(dimethylamino) benzophenone, 200 ml of tetrahydrofuran and 9.3 g (0.03 moles) of sodium acetylide. The reaction mixture was stirred for 24 hours under a nitrogen atmosphere. 3.1 g (0.01 moles ) of additional sodium acetylide were added each time to the reaction mixture after elapsed times of 8 and 16 hours. The reaction mixture was stirred an additional 24 hours, then transfered to a beaker containing a mixture of distilled water and methylene chloride and stirred for 10 minutes. The organic layer was separated and the aqueous layer was extracted twice—each time with 100 ml of methylene chloride. The extracts were combined, dried over anhydrous magnesium sulfate and the solvent removed under vacuum. The product was crystallized using a hexane/ether mixture. The product (4.2 g) melted at 121°–123° C. NMR spectroscopy confirmed the product to be 1-(phenyl)-1-(4-dimethylaminophenyl) -2-propyn-1-ol.

2.0 g (0.008 moles) of the aforedescribed product, 1-(phenyl)-1-(4-dimethylaminophenyl)-2-propyn-1-ol, was added to a reaction flask containing 1.56 g (0.009 mole) of 6-methoxy-2- hydroxynaphthalene and 150 ml of benzene. 5.0 g of acidic alumina was added and the reaction mixture stirred for one hour at room temperature under a nitrogen atmosphere. The reaction mixture was heated on a steam bath for an additional forty-five minutes. The reaction mixture was vacuum filtered to remove the alumina which was washed with 200 ml of ethyl acetate. The ethyl acetate was washed with 250 ml of a 10% aqueous sodium hydroxide solution, dried over anhydrous magnesium sulfate and the solvent was removed under vacuum. The resultant product was crystallized in an ether/hexane mixture. The product (2.0 g) melted at a temperature greater than 225° C. The structure was confirmed by NMR spectroscopy to be 8-methoxy-3-(4-dimethylaminophenyl)-3-(phenyl)-3H-naphtho[2,1-b]pyran.

EXAMPLE 7

A 500 ml round bottom reaction flask was charged with 4.0 g (0.025 mole) of 2,6-dihydroxynaphthalene, 200 ml of methylene chloride and 2.6 g (0.025 mole) of acetic anhydride. One equivalent of triethylamine was slowly added with stirring. After stirring for an additional one hour, dilute hydrochloric acid (200 ml) was added and unreacted 2,6-dihydroxynaphthalene removed by vacuum filtration. The organic phase was separated and the aqueous phase extracted three times, each time with 100 ml of methylene chloride. The extracts were combined, dried and solvent removed under vacuum. The resulting crude oil was a 50—50 mixture of 6-acetoxy-2-hydroxynaphthalene and 2,6-diacetoxynaphthalene.

The crude oil (4.0 g) was mixed with 200 ml of benzene and 2.08 g (0.01 mole) of 1,1-diphenyl-2-propyn-1-ol. A catalytic amount (about 20.0 milligrams) of p-toluene sulfonic acid was added to the mixture with stirring. After 4 hours, a 5 weight percent sodium hydroxide solution was added, the organic phase separated and the aqueous phase extracted three times, each time with 100 ml of methylene chloride. The extracts were combined, dried and solvent removed under vacuum to yield a crude yellow oil. The crude oil was column chromatographed on silica gel using chloroform as the elutant. The solvent was removed from the combined photochromic fractions to yield a crystalline product having a melting point of 180°–182° C. and an assay of 97.7%. NMR spectroscopy confirmed the product to be 8-acetoxy-3,3-diphenyl-3H-naphtho [2,1-b]pyran.

EXAMPLE 8

In addition to the products cited in Examples 1–6, the following compounds were prepared using methods of synthesis similar to those stated in the Examples:

Compound A—3,3-diphenyl-3H-naphtho[2,1-b]pyran,
Compound B—5-methoxy-3,3-diphenyl-3H-naphtho[2,1-b] pyran,
Compound C—7-methoxy-3,3-diphenyl-3H-naphtho[2,1-b] pyran,
Compound D—9-methoxy-3,3-diphenyl-3H-naphtho[2,1-b] pyran,
Compound E—3-(2-fluorophenyl)-3-(4-methoxyphenyl)-3H-naphtho-[2,1-b]pyran.

EXAMPLE 9

All of the compounds of Examples 1–8 were imbibed by thermal transfer into test samples of a homopolymer of diethylene glycol bis(allyl carbonate) by the following procedure. Each naphthopyran was dissolved in toluene solvent to form a 4% solution of the compound. A piece of No. 4 Whatman filter paper was saturated with the naphthopyran solution and allowed to air dry. The dried filter paper was placed on one side of the polymer test sample, which measured ⅛ inch (0.3 centimeter)×2 inch (5.1 centimeters)×2 inch (5.1 centimeters). A piece of untreated filter paper was placed on the other side of the polymer test sample and the resulting sandwich placed between two plates of flat aluminum metal plates. The entire assembly was then placed in a 155° C. oven for a time sufficient to thermally transfer the naphthopyran into the polymer test sample. Residence times in the oven were adjusted to imbibe comparable amounts of the naphthopyran compounds, as measured by UV absorbance.

The imbibed test samples were removed from the oven, washed with acetone, and tested for photochromic s response rates on an optical bench. The samples were illuminated by a filtered 150 watt Xenon lamp fitted with a copper sulfate bath. An OX1 filter with a half-power band width of 320–380 nm was used in conjunction with quartz metallized neutral density filters to provide a total UV irradiance level of 3.0 mW/cm$^2$ as measured using a calibrated radiometer at a position corresponding to the illuminated surface of the sample.

This UV-irradiance level is equivalent to approximately 0.8 sun of a clear noon, July sunshine measured at latitude 41° 10′N using the calibrated radiometer. Control of exposure was facilitated by means of a shutter placed at the exit lens of the Xenon arc lamp housing. A second beam of light provided by a filtered tungsten lamp arranged to pass through the sample area exposed by the UV source was used to monitor changes in transmission of the sample over different wavelength ranges in the visible region of the spectrum. The intensity of the monitoring beam after passing through the sample was measured by means of an IL-1500 radiometer equipped with a silicon detector head and matching filters.

The $\Delta$OD/Min, which represents the sensitivity of the photochromic compound's response to UV light, was measured using photopic filters on the silicon detector. The response of the filtered detector approximated the luminosity curve. The $\Delta$OD was measured over the first five (5) seconds of UV exposure, then expressed on a per minute basis. The saturation optical density (OD) was taken under identical conditions as the $\Delta$OD/Min, except UV exposure was continued for 20 minutes.

The lambda max (UV) reported in Table 4 is the wavelength in the ultraviolet range closest to the visible spectrum. The lambda max (visible) is the wavelength in the visible spectrum at which the maximum absorption of the activated (colored) form of the photochromic compound occurs. The shift in Lambda Max (UV) also results in an unexpected increase in Sensitivity and Saturation 0D (compare the data for Example 1 versus the unsubstituted analog of Example 8A, as well as Example 2 versus Example 8E). Results are tabulated in Table 4.

TABLE 4

| EXAMPLE COMPOUNDS | LAMBDA MAX (VISIBLE) | LAMBDA MAX (UV) | $\Delta$OD/MIN SENSITIVITY | $\Delta$OD @ SATURATION |
|---|---|---|---|---|
| 1 | 473 | 376 | 1.25 | 0.73 |
| 2 | 480 | 376 | 1.21 | 1.46 |
| 3 | 472 | 377 | 0.98 | 0.53 |
| 4 | 467 | 376 | 0.94 | 0.67 |
| 5 | 473 | 375 | 1.12 | 1.47 |
| 6 | 543 | 376 | — | — |
| 7 | 446 | 365 | 0.72 | 0.32 |
| 8A | 430 | 359 | 0.87 | 0.36 |
| 8B | 432 | 323 | 0.49 | 0.46 |
| 8C | 432 | 365 | 0.92 | 0.39 |
| 8D | 426 | 329 | 0.62 | 0.31 |
| 8E | 456 | 359 | 0.98 | 1.00 |

The results of Table 4 show that Compounds 8B, 8C and 8D, which were respectively substituted with a methoxy substituent at the number five, seven and nine carbon atoms on the naphtho portion of the naphthopyran compound, exhibited no significant increase in the measured parameters over the unsubstituted analogous Compound 8A. Compound 1, which was substituted with a methoxy substituent at the number eight carbon atom on the naphtho portion of the naphthopyran compound, demonstrated a surprisingly unexpected increase in all the measured parameters compared to the results obtained for Compounds 8A, 8B, 8C and 8D. Further substitution on the diaryl moieties of Compound 1, i.e., the diphenyl moieties, yielded Compounds 2–6. These compounds also had higher measured results than those obtained for Compounds 8A, 8B, 8C and 8D. Compound 7, which had a substituent different than methoxy at the number 8 carbon atom on the naphtho portion of the naphthopyran compound also exhibited a bathochromic shift in the visible spectrum, but not as large as that of compound 1.

Although the present invention has been described with reference to the specific details of particular embodiments thereof, it is not intended that such details be regarded as limitations upon the scope of the invention except as and to the extent that they are included in the accompanying claims.

I claim:
1. A naphthopyran represented by the following graphic formula:

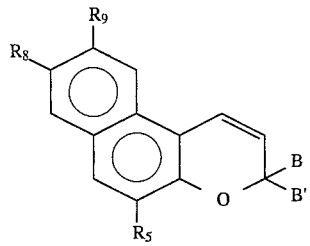

wherein $R_5$ and $R_9$ are each selected from the group consisting of hydrogen, $C_1$–$C_4$ alkoxy, and $C_1$–$C_4$ alkyl; $R_8$ is selected from the group consisting of halogen, $C_1$–$C_5$ acyloxy, benzoyloxy, methoxybenzoyloxy, di($C_1$–$C_5$)alkylamino, and LO—, wherein L is a $C_1$–$C_{12}$ alkyl, $C_6$–$C_9$ aryl($C_1$–$C_3$)alkyl, $C_5$–$C_7$ cycloalkyl, or $C_1$–$C_4$ alkyl substituted $C_5$–$C_7$ cycloalkyl; B is selected from the group consisting of unsubstituted, mono-, di-, or tri- substituted phenyl, said substituents being selected from the group consisting of $C_1$–$C_4$ alkyl, $C_1$–$C_4$ haloalkyl, $C_1$–$C_4$ alkoxy, $C_1$–$C_4$ alkoxy($C_1$–$C_4$)alkyl, di-($C_1$–$C_5$)alkylamino, and halogen, said halogen (halo) substituents being fluorine, chlorine, or bromine; and B' is selected from the group consisting of (i) $C_1$–$C_6$ alkyl, $C_1$–$C_6$ haloalkyl, $C_1$–$C_6$ alkoxy($C_1$–$C_4$)alkyl, said halo group being fluoro or chloro; and (ii) the group represented by the following graphic formula:

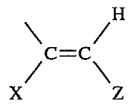

wherein X is hydrogen or $C_1$–$C_4$ alkyl, and Z is selected from the unsubstituted, mono-, and di-substituted members of the group consisting of naphthyl, phenyl, furanyl, and thienyl, said group substituents being $C_1$–$C_4$ alkyl, $C_1$–$C_4$ alkoxy, fluoro, or chloro; or B and B' taken together form a member selected from the group consisting of saturated $C_3$–$C_{12}$ spiro-monocyclic hydrocarbon rings, saturated $C_7$–$C_{12}$ spiro-bicyclic hydrocarbon rings, and saturated $C_7$–$C_{12}$ spiro-tricyclic hydrocarbon rings, provided that B and B' do not form the spiro-tricyclic adamantylidene.

2. A naphthopyran represented by the following graphic formula:

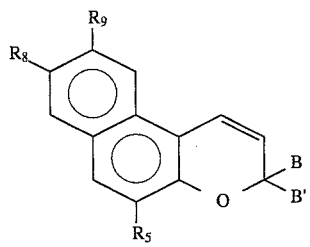

wherein $R_5$ and $R_9$ are each selected from the group consisting of hydrogen, $C_1$–$C_4$ alkoxy, and $C_1$–$C_4$ alkyl; $R_8$ is selected from the group consisting of halogen, $C_1$–$C_5$ acyloxy, benzoyloxy, methoxybenzoyloxy, di($C_1$–$C_5$)alkylamino, and LO—, wherein L is a $C_1$–$C_{12}$ alkyl, $C_6$$C_9$ aryl($C_1$–$C_3$)alkyl, $C_5$–$C_7$ cycloalkyl, or $C_1$–$C_4$ alkyl substituted $C_5$–$C_7$ cycloalkyl; B is selected from the group consisting of phenyl and the group represented by the following graphic formula:

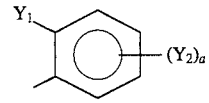

wherein $Y_1$ is selected from the group consisting of $C_1$–$C_5$ alkyl, $C_1$–$C_5$ alkoxy, fluoro and chloro; $Y_2$ is selected from the group consisting of $C_1$–$C_5$ alkyl, $C_1$–$C_5$ alkoxy, cyano, hydroxy, halogen, acrylyl, methacrylyl, acryloxy ($C_1$–$C_4$) alkyl, and methacryloxy ($C_1$–$C_4$) alkyl; a is an integer of from 0 to 2; said halogen (halo) substituents being fluorines chlorine, or bromine; and B' is selected from the group consisting of (i) $C_1$–$C_6$ alkyl, $C_1$–$C_6$ haloalkyl, $C_1$–$C_6$ alkoxy($C_1$–$C_4$)alkyl, said halo group being fluoro or chloro; and (ii) the group represented by the following graphic formula:

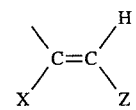

wherein X is hydrogen or $C_1$–$C_4$ alkyl, and Z is selected from the unsubstituted, mono-, and di-substituted members of the group consisting of naphthyl, phenyl, furanyl, and thienyl, said group substituents being $C_1$–$C_4$ alkyl, $C_1$–$C_4$ alkoxy, fluoro, or chloro; or B and B' taken together form a member selected from the group consisting of saturated $C_3$–$C_{12}$ spiro-monocyclic hydrocarbon rings, saturated $C_7$–$C_{12}$ spiro-bicyclic hydrocarbon rings, and saturated $C_7$–$C_{12}$ spiro-tricyclic hydrocarbon rings, provided that B and B' do not form the spiro-tricyclic adamantylidene.

3. The naphthopyran of claim 2 wherein $R_5$ and $R_9$ are each selected from the group consisting of hydrogen, $C_1$–$C_3$ alkoxy, and $C_1$–$C_3$ alkyl; $R_8$ is selected from the group consisting of chloro, bromo, $C_1$–$C_4$ acyloxy, benzoyloxy, methoxybenzoyloxy, di($C_1$–$C_4$)alkylamino, and LO—, wherein L is a $C_1$–$C_{10}$ alkyl, $C_6$–$C_7$ aryl ($C_1$–$C_2$)alkyl, $C_5$–$C_6$ cycloalkyl, or $C_1$–$C_3$ alkyl substituted $C_5$–$C_6$ cycloalkyl; B is selected from the group consisting of phenyl and the group represented by the following graphic formula:

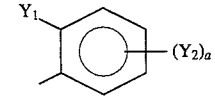

wherein $Y_1$ is a $C_1$–$C_3$ alkyl, $C_1$–$C_3$ alkoxy, or fluoro; $Y_2$ is a $C_1$–$C_3$ alkyl, $C_1$–$C_3$ alkoxy, or fluoro; a is the integer 0 or 1; and B' is selected from the group consisting of (i) $C_1$–$C_4$ alkyl; and (ii) the group represented by the following graphic formula:

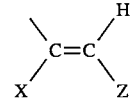

wherein X is hydrogen or methyl, and Z is phenyl or mono-substituted phenyl, said substituents being $C_1$–$C_3$ alkyl, $C_1$–$C_3$ alkoxy, and fluoro; or B and B' taken together form a member selected from the group consisting of saturated $C_3$–$C_8$ spiro-monocyclic hydrocarbon rings, saturated $C_7$–$C_{10}$ spiro-bicyclic hydrocarbon rings, and saturated $C_7$–$C_{10}$ spiro-tricyclic hydrocarbon rings.

4. The naphthopyran of claim 2 wherein $R_5$ and $R_9$ are each selected from the group consisting of hydrogen, $C_1$–$C_2$ alkoxy, and $C_1$–$C_2$ alkyl; and $R_8$ is selected from the group consisting of bromo, $C_1$–$C_3$ acyloxy, di($C_1$–$C_3$)alkylamino, and LO—, wherein L is a $C_1$–$C_4$ alkyl or $C_1$–$C_2$ alkyl substituted $C_5$–$C_6$ cycloalkyl; and B and B' taken together form bornylidene, norbornylidene, or bicyclo[3.3.1]nonan-9-ylidene.

5. The naphthopyran of claim 4 wherein $R_8$ is methoxy and the position of $Y_2$ is meta or para to the carbon atom attached to the pyran ring when a is 1.

6. A photochromic article comprising a polymeric organic host material and a photochromic amount of a naphthopyran compound of claim 1.

7. The photochromic article of claim 6 wherein the polymeric organic host material is selected from the group consisting of polyacrylates, polymethacrylates, poly($C_1$–$C_{12}$ alkyl methacrylates), polyoxy(alkylene methacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

8. A photochromic article comprising a polymeric organic host material and a photochromic amount of a naphthopyran compound of claim 2.

9. The photochromic article of claim 8 wherein the polymeric organic host material is selected from the group consisting of polyacrylates, polymethacrylates, poly($C_1$–$C_{12}$ alkyl methacrylates), polyoxy(alkylene methacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), s copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

10. The photochromic article of claim 9 wherein the polymeric organic host material is a solid transparent homopolymer or copolymer selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis-(allyl carbonate) monomers, diethylene glycol dimethacrylate monomers, diisopropenyl benzene monomers, and ethoxylated trimethylol propane triacrylate monomers.

11. The photochromic article of claim 10 wherein the photochromic compound is present in an amount of from about 0.05 to 1.0 milligram per square centimeter of organic host material surface to which the photochromic substance(s) is incorporated or applied.

12. The photochromic article of claim 11 wherein the article is a lens.

13. A photochromic article comprising a photochromic amount of the naphthopyran compound of claim 3 and a polymeric organic host material selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis-(allyl carbonate) monomers, diethylene glycol dimethacrylate monomers, diisopropenyl benzene monomers, and ethoxylated trimethylol propane triacrylate monomers.

14. A photochromic article comprising a photochromic amount of the naphthopyran compound of claim 5 and a polymeric organic host material selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis-(allyl carbonate) monomers, diethylene glycol dimethacrylate monomers, diisopropenyl benzene monomers, and ethoxylated trimethylol propane triacrylate monomers.

15. A photochromic article comprising, in combination, a photochromic amount of each of (a) at least one naphthopyran compound of claim 1, and (b) at least one other organic photochromic compound having at least one activated absorption maxima within the range of between about 400 and 700 nanometers and a polymeric organic host material selected from the group consisting of poly(methyl methacrylate), poly(ethylene glycol bis methacrylate), poly-(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, diisopropenyl benzene monomers, and ethoxylated trimethylol propane triacrylate monomers.

16. A photochromic article comprising, in combination, a solid transparent polymeric organic host material, and a photochromic amount of each of (a) at least one naphthopyran compound of claim 2, and (b) at least one other organic photochromic compound having at least one activated absorption maxima within the range of between about 400 and 700 nanometers.

17. The photochromic article of claim 16 wherein the polymeric organic host material is selected from the group consisting of polyacrylates, polymethacrylates, poly($C_1$–$C_{12}$ alkyl methacrylates), polyoxy(alkylene methacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

18. The photochromic article of claim 17 wherein the organic photochromic compound (b) is selected from the group consisting of:
(a) organic photochromic substances having at least one absorption maximum in the visible range of between 400 and less than 500 nanometers;
(b) organic photochromic substances having an absorption maximum within the visible range of between about 400 and 500 nanometers and an absorption maximum within the visible range of between 500 and 700 nanometers; and
(c) organic photochromic substances having an activated absorption maxima in the visible range of greater than 570 nanometers; and
(d) mixtures of said organic photochromic substances.

19. The photochromic article of claim 18 wherein the polymeric organic host material is a solid transparent homopolymer or copolymer selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, diisopropenyl benzene monomers, and ethoxylated trimethylol propane triacrylate monomers.

20. The photochromic article of claim 16 wherein the organic photochromic compound (b) is selected from the group consisting of spiro(indoline)naphthoxazines, spiro(indoline)-pyridobenzoxazines, spiro(benzindoline)pyridobenzoxazines, spiro(benzindoline)naphthoxazines, spiro(benzindoline)naphthopyrans, spiro(indoline)benzoxazines, spiro(indoline)benzopyrans, spiro(indoline)naphthopyrans, spiro(indoline)quinopyrans, spiro(indoline)pyrans, 3H-naphtho[2,1-b]pyrans, 2H-phenanthro[4,3-b]pyrans; 3H-phenanthro[1,2-b]pyrans; benzopyran compounds and mixtures of such photochromic substances.

21. A photochromic article comprising, in combination, a photochromic amount of each of (a) at least one naphthopyran compound of claim 3, and (b) at least one other organic photochromic compound having at least one activated absorption maxima within the range of between about 400 and 700 nanometers and a polymeric organic host material selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, diisopropenyl benzene monomers, and ethoxylated trimethylol propane triacrylate monomers.

22. A photochromic article comprising, in combination, a photochromic amount of each of (a) at least one naphthopyran compound of claim 5, and (b) at least one other organic photochromic compound having at least one activated absorption maxima within the range of between about 400 and 700 nanometers and a polymeric organic host material selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, diisopropenyl benzene monomers, and ethoxylated trimethylol propane triacrylate monomers.

* * * * *